(12) United States Patent
Fologea

(10) Patent No.: US 12,208,138 B2
(45) Date of Patent: Jan. 28, 2025

(54) RADIATION-TRIGGERED LIPOSOMES

(71) Applicant: BOISE STATE UNIVERSITY, Boise, ID (US)

(72) Inventor: Daniel Fologea, Boise, ID (US)

(73) Assignee: BOISE STATE UNIVERSITY, Boise, ID (US)

( * ) Notice: Subject to any disclaimer, the term of this patent is extended or adjusted under 35 U.S.C. 154(b) by 1137 days.

(21) Appl. No.: 16/971,158

(22) PCT Filed: Feb. 18, 2019

(86) PCT No.: PCT/US2019/018400
§ 371 (c)(1),
(2) Date: Aug. 19, 2020

(87) PCT Pub. No.: WO2019/161325
PCT Pub. Date: Aug. 22, 2019

(65) Prior Publication Data
US 2020/0405857 A1    Dec. 31, 2020

Related U.S. Application Data

(60) Provisional application No. 62/632,123, filed on Feb. 19, 2018.

(51) Int. Cl.
| | | |
|---|---|---|
| A61K 41/00 | (2020.01) |
| A61K 9/127 | (2006.01) |
| A61K 38/16 | (2006.01) |
| A61K 38/17 | (2006.01) |
| A61N 5/06 | (2006.01) |
| A61N 5/10 | (2006.01) |

(52) U.S. Cl.
CPC ........ *A61K 41/0038* (2013.01); *A61K 9/1272* (2013.01); *A61K 9/1273* (2013.01); *A61K 38/164* (2013.01); *A61K 38/1767* (2013.01); *A61N 5/0601* (2013.01); *A61N 2005/0661* (2013.01); *A61N 2005/1098* (2013.01)

(58) Field of Classification Search
CPC .............. A61K 41/0038; A61K 9/1272; A61K 9/1273; A61K 38/164; A61K 38/1767; A61N 5/0601; A61N 2005/0661; A61N 2005/1098
See application file for complete search history.

(56) References Cited

U.S. PATENT DOCUMENTS

| | | | | |
|---|---|---|---|---|
| 6,004,534 A | * | 12/1999 | Langer .................. | A61K 9/1273 424/9.4 |
| 2007/0207973 A1 | * | 9/2007 | Daifuku ............... | C07D 515/22 536/27.1 |
| 2011/0190623 A1 | | 8/2011 | Li et al. | |
| 2012/0043275 A1 | | 2/2012 | Montemagno et al. | |
| 2014/0328905 A1 | * | 11/2014 | Fologea ............... | A61K 9/1271 424/130.1 |
| 2016/0282369 A1 | * | 9/2016 | Cravatt .............. | G01N 33/6842 |

FOREIGN PATENT DOCUMENTS

| | | | | |
|---|---|---|---|---|
| CN | 101199505 A | * | 6/2008 | |
| WO | WO-2005005570 A1 | * | 1/2005 | ........... C07D 311/92 |
| WO | WO-2010114901 A1 | * | 10/2010 | ........... A61K 9/0009 |
| WO | WO-2017120537 A1 | * | 7/2017 | ........... A61K 31/337 |

OTHER PUBLICATIONS

Machine translation of CN-101199505-A (Year: 2008).*
Sezgin et al.; The mystery of membrane organization: composition, regulation and roles of lipid rafts; © 2017 Macmillan Publishers Limited; Nature Reviews | Molecular Cell Biology vol. 18 | Jun. 2017 | 361-373 (Year: 2017).*
Haberkant et al.; Bifunctional Sphingosine for Cell-Based Analysis of Protein-Sphingolipid Interactions; ACS Publications; ACS Chem. Biol. 2016, 11, 222-230 (Year: 2016).*
El-Mezayen et al.; Hepatic stellate cell-targeted imatinib nanomedicine versus conventional imatinib: A novel strategy with potent efficacy in experimental liver fibrosis; Elsevier; Journal of Controlled Release 266 (2017) 226-237 (Year: 2017).*
Lian et al.; Trends and Developments in Liposome Drug Delivery Systems; Wiley-Liss, Inc. and the American Pharmaceutical Association; Journal of Pharmaceutical Sciences, vol. 90, No. 6, Jun. 2001 667-680 (Year: 2001).*
Diazirine; https://enamine.net/public/MedChem/Enamine-CF3-diazirines-for-photoaffinity-labeling-2022.pdf (site accessed Apr. 2024) (Year: 2022).*
DSPC; Serge Shahinian, John R. Silvius, in Methods in Enzymology, 2004; In Liposomes, Part D (Year: 2004).*
PCT Search Report and Written Opinion prepared for PCT/US2019/018400, completed Apr. 18, 2019.

* cited by examiner

Primary Examiner — Robert A Wax
Assistant Examiner — John W Lippert, III
(74) Attorney, Agent, or Firm — Barnes & Thornburg LLP

(57) ABSTRACT

The present disclosure is directed to radiation triggered liposomes and their use in delivery and release of pharmaceutical drugs upon exposure to ionizing radiation. In one embodiment liposomes are provided that comprise cholesterol and sphingolipids modified to comprise reactive groups that are activated by ionizing radiation to form crosslinks with other lipids of the liposome causing the release of the liposomal contents.

20 Claims, 5 Drawing Sheets

DSPC.

Cholesterol

Sphingosine

P-Cholesterol

P-Sphingosine

RADIATION-TRIGGERED LIPOSOMES

CROSS REFERENCE TO RELATED APPLICATIONS

This application is a U.S. national stage application under 35 U.S.C. § 371 (b) of International Application No. PCT/US2019/018400 filed Feb. 18, 2019, which claims priority to U.S. Provisional Patent Application No. 62/632,123 filed on Feb. 19, 2018, the disclosures of both of which are hereby expressly incorporated by reference in its entirety.

BACKGROUND OF THE DISCLOSURE

Liposomes are self-assembled vesicles having a spherical bilayer structure surrounding an aqueous core domain. Liposomes can range in size from about 20 and about 30,000 nm in diameter and can be unilaminate or multilaminate (i.e., comprising concentric lipid bilayers). Typically, liposomes can be divided into three categories based on their overall size and the nature of the lamellar structure. The three classifications, as developed by the New York Academy Sciences Meeting, "Liposomes and Their Use in Biology and Medicine," of December 1977, are multi-lamellar vesicles (MLV's), small uni-lamellar vesicles (SUV's) and large uni-lamellar vesicles (LUV's).

Liposome have been previously disclosed for use as delivery vehicles that are capable of carrying both hydrophobic cargo in the lipid bilayer and/or hydrophilic cargo in the aqueous core. Liposome size is usually in a range from about 50 to about 250 nm, which is particularly suitable for targeted delivery of chemotherapy agents to solid tumor sites via the enhanced permeability and retention of cancer tissues (the EPR effect) (Maeda, H., et al., J. Controlled Release. 65(1-2): 271 (2000)). The preferential accumulation of drug-containing liposomes at the tumor site via EPR provides a means for localizing the drug, improving drug efficacy, and reducing drug toxicity to normal cells or tissues. For example, Doxil™, an FDA-approved liposome product containing doxorubicin, has been shown to have reduced toxicity compared with the free drug (Martin, F. J., et al., "Clinical pharmacology and antitumor efficacy of DOXIL." Medical Applications of Liposomes. Ed. D. D. Lasic. Amsterdam: Elsevier, 1998, pp 635-688).

However, the benefits of liposomal drug delivery vehicles are limited by drawbacks including liposome metabolism and excretion from the body. In particular, optimizing the release rate of a liposomal drug is a difficult balancing act between in vivo half life and release. In general, leaky liposomes will make the encapsulated drug more available, but cause more risk in toxicity similar to the free drug. On the other hand, less leaky liposomes may reduce toxicity, but they may not provide the desirable drug release for efficacy. Thus while liposomes are already used for cancer treatment, the efficacy of such treatments is hampered by the lack of an effective mechanism to trigger the release of the incorporated drug.

Various triggering mechanisms have been proposed to release liposome content upon delivery to a target site. These mechanisms include temperature triggered release (US 20070264322), use of nano particles (US 20130028962) use of trigger polypeptides (US 20060210549) and the use of photopolymerization. An extensive review of methods to photochemically reorganize lipid bilayers has been published (O'Brien et al., Bioorganic Photochemistry 1993, 2:111-167). Previous work from other groups indicates that a more rigid membrane realized by cross-linking a small amount of photo-polymerizable lipids increases permeability to drug-like molecules entrapped in the liposome (see U.S. Pat. No. 8,535,712). However, this system discloses the use of photo-polymerizable lipids that are distributed evenly throughout the liposome membrane, thus limiting the impact of the induced crosslinking.

Accordingly, there is still a need for a liposome delivery vehicle that has sufficient stability to allow for effective delivery to a target site while having a triggering mechanism that effectively releases the liposomal content at the target site.

SUMMARY

The present disclosure is directed to the use of polymerizable components that will cluster upon inclusion in a liposome and will cause the liposome to release their contents upon exposure to radiation, including for example exposure to UV rays or X rays. More particularly, the polymerizable components may comprise cholesterol and/or sphingolipid/glycosphingolipid components of the liposome that are modified to comprise a reactive group (e.g., a diazirine) that upon activation by radiation will form a covalent bond with other components of the lipid bilayer of the liposome to induce release of the liposome contents.

Unlike previously disclosed triggering mechanisms that use radiation and photo-sensitive lipids, the polymerizable cholesterol and polymerizable sphinoglipids compounds of the presently disclosed liposomes accumulate primarily into lipid rafts, which significantly facilitate cross linking upon exposure to radiation and thus produced an improved efficacy with respect to drug release. In one embodiment, the liposome further comprises a therapeutic agent entrapped in the lipid bilayer or within the lumen of the liposome.

In accordance with one embodiment a radiation triggered liposome is provided wherein the liposome comprises a liposome forming lipid (e.g., a phospholipid) and a polymerizable lipid bilayer component that accumulates primarily into lipid rafts. The polymerizable lipid bilayer component comprises one or more reactive groups that upon activation by ionizing radiation form covalent bonds with other components (lipids and proteins) of the liposome. The liposome-forming lipid component of the present radiation triggered liposomes comprises one or more standard lipids known to those skilled in the art for preparing liposomes. For example lipids known to form stable liposomes include, but are not limited to, phosphatidylcholine (PC), phosphatidylethanolamine (PE), phosphatidic acid (PA), phosphatidylglycerol (PG), phospatidylserine PS) and phosphatidylinositol (PI), and non-natural lipid(s) and cationic lipid(s) such as DOTMA (N-(1-(2,3-dioxyloxy)propyl)-N,N,N-trimethyl ammonium chloride) and 1,2-distearoyl-sn-glycero-3-phosphocholine (DSPC).

In accordance with one embodiment, the polymerizable lipid bilayer component of the present radiation triggered liposomes, that has been selected for exhibiting the ability to accumulate primarily into lipid rafts, comprises a) a steroid that has been modified to comprise a reactive group that upon activation by ionizing radiation forms covalent bonds with other lipids of the liposome, b) a sphingolipid/glycosphingolipid that has been modified to comprise a reactive group that upon activation by ionizing radiation forms covalent bonds with other lipids of the liposome, or c) both a) and b). In a further embodiment the polymerizable lipid bilayer component is a cholesterol and/or sphingolipid that has been modified to comprise one or more diazirine reactive groups. More particularly, in one embodiment the polymerizable sphingolipid is selected from the group consisting of sphingosine, ceramide, sphingomyelin, cerebroside and ganglioside that has been modified to comprise one or more diazirine groups on the hydrophobic chain of the sphingolipid.

In one embodiment the liposomes of the present disclosure further comprise an unpolymerizable sterol component, including for example cholesterol or known derivatives thereof. In accordance with one embodiment the liposome further comprises a lipid raft associating polypeptide, including for example the non-virulent part of the cholera toxin (cholera toxin subunit B) or lysenin. Such lipid raft associating proteins further contribute to raft stabilization and therefore improved cross linking and release upon radiation exposure.

In one embodiment, the liposome also contains a nano-scintillator that is responsive to radiation. In this embodiment, the target is exposed to radiation, such as X-rays, to cause the nano-scintillators to emit UV light. The emitted UV light enhances the activation of a reactive group present on polymerizable cholesterol and/or sphingolipids of the liposome lipid bilayer resulting in further crosslinking of the membrane components of the lipid bilayer and enhanced release of the liposome contents. In one embodiment the reactive group present on the polymerizable cholesterol or polymerizable sphingolipid is a diazirine group.

In one embodiment the liposome comprise a therapeutic agent entrapped in the liposome, either embedded in the lipid bilayer or located in the aqueous lumen of the liposome. Examples of therapeutic agents include, but are not limited to, chemotherapeutics, biological response modifiers, biological cofactors, pharmaceuticals and radiopharmaceuticals, cell toxins, and radiation sensitizers. In one embodiment the entrapped therapeutic is a chemotherapeutic agent, an antibody, a toxin, or any combination thereof. In one embodiment the therapeutic agent is imiquinod. The present disclosure also encompasses pharmaceutical compositions comprising any of the radiation triggered liposomes of the present disclosure and a pharmaceutically acceptable carrier.

In one embodiment a method of localized delivery of a therapeutic agent is provided. The method comprises the steps of administering to a patient in need of therapy, a composition comprising a radiation triggered liposome of the present disclosure. After passage of a sufficient amount of time to allow the administered radiation triggered liposomes to become concentrated at the target tissue, the target tissue is irradiated with ionizing radiation sufficient to affect activation of the reactive groups on the lipid raft associated compounds resulting in crosslinking of the lipid bilayer components and release of the lipid contents. In one embodiment the ionizing radiation is X ray irradiation. The radiation triggered liposomes accumulate in the target tissues either passively or can be targeted to the desired location using techniques known to those skilled in the art.

In accordance with one embodiment a method of enhancing ionizing radiation therapy in the treatment of cancer in a human patient is provided. The method comprises the steps of administering to the patient any of the radiation triggered liposomes disclosed herein, wherein said liposome entraps an anti-cancer therapeutic. After a sufficient time has passed to allow the administered radiation triggered liposomes to accumulate in the target tissues, either passively or by targeting using techniques known to those skilled in the art, ionizing radiation therapy is then administered to target a tumor site of the patient. The ionizing radiation (e.g., x-rays) thereby destabilizes the membrane of said administered radiation triggered liposome to release the anti-cancer therapeutic at the targeted site to complement the therapeutic radiation therapy and enhance the efficacy of the ionizing radiation therapy.

In a further embodiment, a kit is provided for preparing radiation triggered liposomes of the present disclosure. The kit comprises a liposome forming lipid (e.g., a phospholipid) and a polymerizable lipid bilayer component that accumulates primarily into lipid rafts, wherein the polymerizable lipid bilayer component comprises a reactive group that is activated by ionizing radiation.

BRIEF DESCRIPTION OF THE DRAWINGS

FIG. 1A), Cholesterol (Chol; FIG. 1B), and Sphingomyelin (SM; FIG. 1C).

FIG. 2A), and Photo click sphingosine (P-SM; FIG. 2B).

DETAILED DESCRIPTION

Definitions

Figure 1A:
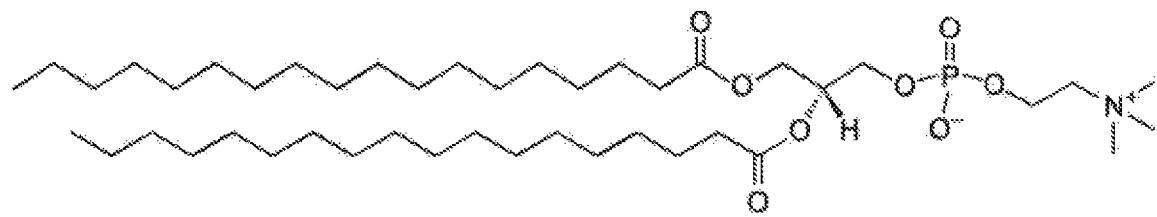
FIGS. 1A-1C provides the structure of typical lipid bilayer components 1,2-distearoyl-sn-glycero-3-phosphocholine (DSPC.

In describing and claiming the invention, the following terminology will be used in accordance with the definitions set forth below.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

As used herein, the term "treating" includes prophylaxis of the specific disorder or condition, or alleviation of the symptoms associated with a specific disorder or condition and/or preventing or eliminating said symptoms. For example, as used herein the term "treating cancer" will refer in general to reducing tumor size or preventing further growth or spread of neoplastic tissues as well as elimination of detectable cancer cells.

As used herein an "effective" amount or a "therapeutically effective amount" of a therapeutic agent refers to a sufficient amount of the agent to provide the desired effect. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route such as subcutaneous, intramuscular, intraspinal, or intravenous.

As used herein, the term "purified" and like terms relate to the isolation of a molecule or compound in a form that is substantially free of contaminants normally associated with the molecule or compound in a native or natural environment. As used herein, the term "purified" does not require absolute purity; rather, it is intended as a relative definition. The term "purified polypeptide" is used herein to describe a polypeptide which has been separated from other compounds including, but not limited to nucleic acid molecules, lipids and carbohydrates.

The term "isolated" requires that the referenced material be removed from its original environment (e.g., the natural environment if it is naturally occurring). For example, a naturally-occurring polynucleotide present in a living animal is not isolated, but the same polynucleotide, separated from some or all of the coexisting materials in the natural system, is isolated.

As used herein, the term "peptide" encompasses a sequence of 3 or more amino acids and typically less than 50 amino acids, wherein the amino acids are naturally occurring or non-naturally occurring amino acids. Non-naturally occurring amino acids refer to amino acids that do not naturally occur in vivo but which, nevertheless, can be incorporated into the peptide structures described herein.

As used herein, the terms "polypeptide" and "protein" are terms that are used interchangeably to refer to a polymer of amino acids, without regard to the length of the polymer. Typically, polypeptides and proteins have a polymer length that is greater than that of "peptides."

As used herein an amino acid "substitution" refers to the replacement of one amino acid residue by a different amino acid residue.

As used herein, the term "conservative amino acid substitution" is defined herein as exchanges within one of the following five groups:

I. Small aliphatic, nonpolar or slightly polar residues:
   Ala, Ser, Thr, Pro, Gly;
II. Polar, negatively charged residues and their amides and esters:
   Asp, Asn, Glu, Gln, cysteic acid and homocysteic acid;
III. Polar, positively charged residues:
   His, Arg, Lys; Ornithine (Orn)
IV. Large, aliphatic, nonpolar residues:
   Met, Leu, Ile, Val, Cys, Norleucine (Nle), homocysteine
V. Large, aromatic residues:
   Phe, Tyr, Trp, acetyl phenylalanine As used herein a general reference to a peptide is intended to encompass peptides that have modified amino and carboxy termini. For example, an amino acid chain comprising an amide group in place of the terminal carboxylic acid is intended to be encompassed by an amino acid sequence designating the standard amino acids.

As used herein, the term "alkyl" refers to a linear or branched hydrocarbon containing the indicated number of carbon atoms. Exemplary alkyls include methyl, ethyl, and linear propyl groups. The designation $C_1$-$C_n$ alkyl is an abbreviation designating an alkyl chain having one to "n" carbons in the hydrocarbon chain.

As used herein, the term "heteroalkyl" refers to a linear or branched hydrocarbon containing the indicated number of carbon atoms and at least one heteroatom in the backbone of the structure. Suitable heteroatoms for purposes herein include but are not limited to N, S, and O.

As used herein, the term "cycloalkyl" refers to a cyclic hydrocarbon group containing the indicated number of carbon atoms, e.g., cyclopropyl, cyclobutyl, cyclohexyl, and cyclopentyl.

As used herein, the term "heterocyclic" refers to a cyclic hydrocarbon group containing the indicated number of carbon atoms and one to three heteroatoms independently selected from the group consisting of oxygen, nitrogen, and sulfur. Nonlimiting examples of heterocycloalkyl groups include piperdine, tetrahydrofuran, tetrahydropyran, dihydrofuran, morpholine, thiophene, and the like.

As used herein, the term "aryl" refers to a monocyclic or polycyclic aromatic group, preferably a monocyclic or bicyclic aromatic group, e.g., phenyl or naphthyl, containing the indicated number of carbon atoms. Unless otherwise indicated, an aryl group can be unsubstituted or substituted.

As used herein, the term "heteroaryl" refers to a monocyclic or polycyclic aromatic group containing the indicated number of carbon atoms and at least one heteroatom selected from the group consisting of oxygen, nitrogen, and sulfur. Unless otherwise indicated, an aryl group can be unsubstituted or substituted.

As used herein the term "photo click" defines a reactive group on a compound, wherein the reactive group becomes activated upon stimulation by a radiation source to induce a biocompatible small molecule reaction that covalently links the compound having the reactive group to another compound. Accordingly, a "photo click compound" is a compound that comprises one or more photo click reactive groups.

As used herein the term "radiation" or "radiation source" encompasses the emission of energy as electromagnetic waves or as moving subatomic particles, especially high-energy particles that cause ionization. Examples of radiation include but are not limited to UV rays, X-rays, beta particles, and gamma rays. Ionizing radiation consisting of UV rays, X-rays, beta particles, or gamma rays with sufficient energy to cause ionization in the medium through which it passes.

The term "lipid" or "liposomal forming lipid", as referred to herein, means a long-chain molecule comprised of fatty acids that may form liposomes under suitable liposome forming conditions. Examples of such lipids include, but are not limited to, phosphatidylcholine (PC), phosphatidylethanolamine (PE), phosphatidic acid (PA), phosphatidylglycerol (PG), and nonnatural lipid(s) and cationic lipid(s) such as DOTMA (N-(1-(2,3-dioxyloxy)propyl)-N,N,N-trimethyl ammonium chloride) and 1,2-distearoyl-sn-glycero-3-phosphocholine (DSPC).

The term "liposome" refers to a microscopic vesicle comprising lipid bilayer(s). Structurally, liposomes range in size and shape from long tubes to spheres and can be as small as 25 nm and as large as 500 nm in diameter.

As used herein the term "lipid raft" or "lipid components that accumulate in rafts" defines subdomains of a liposome lipid bilayer that contain high concentrations of cholesterol, sphingolipids and glycosphingolipids. The fatty-acid side chains of the lipids present in lipid rafts tend to be more highly saturated than those in the surrounding membrane. They exist as distinct liquid-ordered regions of the membrane that are resistant to extraction with nonionic detergents. Bulk plasma membrane contains more phospholipids with unsaturated acyl chains. As a result, bulk plasma membrane is more fluid than lipid rafts.

As used herein the term "lipid raft associated moiety" encompasses lipids, proteins and steroids that predominantly cluster together in a lipid bilayer.

A "polymerizable lipid", as used herein, is a lipid that has at least one radiation activatable group incorporated somewhere along its lipid chains. Examples of polymerizable lipids include "polymerizable sphingolipids" and "polymerizable glycospingolipids". In one embodiment the radiation activatable group is a diazirine group.

A "radiation triggered liposome" is a liposome that comprises liposome forming lipids as well as polymerizable lipids wherein the liposome has an enhanced release of its liposomal contents upon exposure to a stimulating amount of radiation.

An "ionizing radiation polymerizable lipid" is a lipid that comprises a reactive group that upon exposure to ionizing radiation will induce formation of a covalent bond between the reactive group and a substituent of another compound.

A "polymerizable steroid", as used herein, is a steroid that has at least one radiation activatable group covalently linked to the steroid.

As used herein the term "radiation activatable group" is a functional group that when contacted with a stimulating amount of radiation will induce formation of a covalent bond between the radiation activatable group and a substituent of another compound.

Embodiments

The present disclosure is directed to liposomes that comprise polymerizable lipid raft associated moieties, wherein the polymerizable lipid raft associated moieties comprise reactive moieties that upon irradiation will covalently bond with other components of the liposome bilayer. In accordance with one embodiment the radiation triggered liposomes of the present disclosure are small uni-lamellar vesicles (SUV's) ranging in size from about 50 to about 250 nm in diameter. In one embodiment the liposomes have a diameter within the range of about 100 to 200 nm.

In accordance with one embodiment the polymerizable lipid raft associating components of the radiation triggered liposomes are selected from the group consisting of polymerizable sphingolipids, polymerizable glycosphingolipids or polymerizable steroids. The polymerizable lipid raft associating components represent a minor component of the liposome relative to the stable liposome-forming lipid component that lacks the reactive moieties. More particularly, the ratio of standard liposome-forming lipid to polymerizable lipid raft associated moieties can be about 7:1, 6:1, 5:1, 4:1 or 3:1.

A host of reactive moieties can be utilized to modify sphingolipids and steroids to make them polymerizable. These groups include diacetylene, acryloyl, methacryloyl, itaconyl, dienoyl, diazirine, sorbyl, muconyl, styryl, vinyl, thiol (or lipoyl), and chain terminal isocyanates. In one embodiment the reactive moiety is a diazirine group.

In one embodiment a liposome is provided that comprises
a) a polymerizable sphingolipid;
b) a polymerizable glycospingolipid;
c) a polymerizable steroid;
d) the combination of a) and b);
e) the combination of a) and c);
f) the combination of b) and c); or
g) the combination of a), b) and c), wherein the total content of polymerizable lipid raft associated moieties is less than 30%, less than 25% or less than 20%. In one embodiment the polymerizable steroid is a polymerizable cholesterol, or polymerizable cholesterol derivative.

In one embodiment the polymerizable steroid is a compound of the general structure:

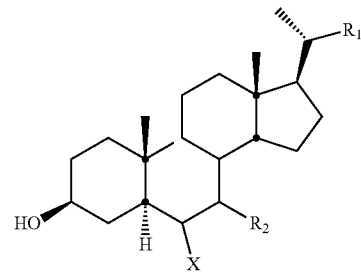

wherein X is a radiation activatable group;
$R_1$ is selected from the group consisting of $C_1$-$C_8$, ($C_1$-$C_8$)OH, $(CH_2CH_2CHOHCH(CH_3)_2$, $CH_2CH_2CH_2COH(CH_3)_2$, $CH_2CH_2CH_2CHOHCH_3$, $(CH_2)_2COO(CH_2)_5CH_3$ and $(CH_2)_2COO(CH_2)_4CHCH$, and
$R_2$ is H or OH. In one embodiment the polymerizable steroid is a compound of the general structure:

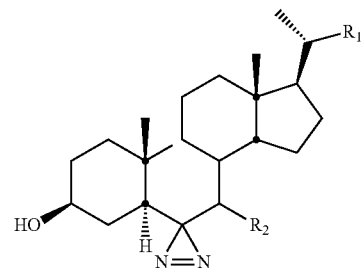

wherein $R_1$ is selected from the group consisting of $C_1$-$C_8$, ($C_1$-$C_8$)OH, $(CH_2CH_2CHOHCH(CH_3)_2$, $CH_2CH_2CH_2COH(CH_3)_2$, $CH_2CH_2CH_2CHOHCH_3$, $(CH_2)_2COO(CH_2)_5CH_3$ and $(CH_2)_2COO(CH_2)_4CHCH$, and $R_2$ is H or OH. More particularly in one embodiment the polymerizable steroid is a compound of the general structure:

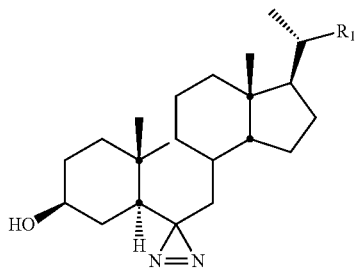

wherein $R_1$ is selected from the group consisting of $C_1$-$C_8$, $(C_1$-$C_8)OH$, $(CH_2)_2COO(CH_2)_4CH_3$ and $(CH_2)_2COO(CH_2)_4CH$. In one embodiment $R_1$ is $CH_2CH_2CH_2CH(CH_3)_2$, $(CH_2)_2COO(CH_2)_5CH_3$ or $(CH_2)_2COO(CH_2)_4CHCH$. In one embodiment the polymerizable steroid is a compound of the general structure:

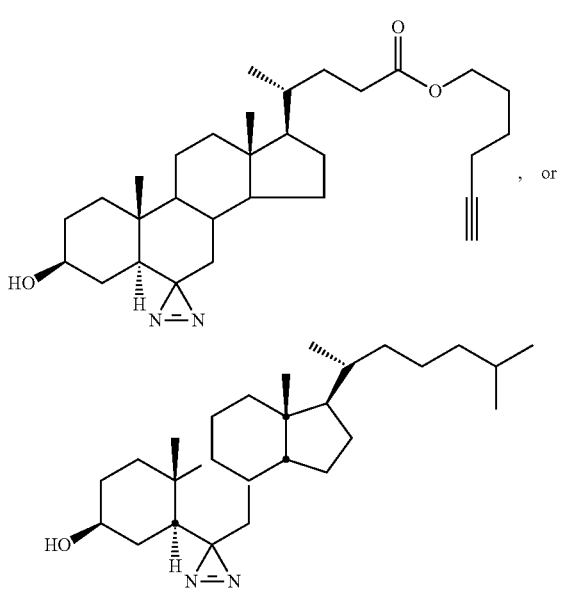

In one embodiment the polymerizable sphingolipid or glycospingolipid is a compound of the general structure:

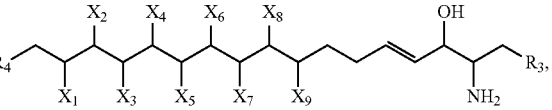

wherein $X_1$-$X_9$ are independently H or a radiation activatable group;

$R_3$ is OH, phosphocholine, phosphoenthanolamine, or a carbohydrate; and $R_4$ is —$CH_2CH_3$ or —CCH. In one embodiment 1, 2, or 3 of $X_1$-$X_9$ are radiation activatable groups with the remainder being H. In one embodiment the radiation activatable group is a diazirine group. In one embodiment the polymerizable sphingolipid is selected from the group consisting of sphingosine, ceramide, sphingomyelin, cerebroside and ganglioside modified to comprise one or more diazirine groups on the hydrophobic chain of the sphingolipid.

In one embodiment the polymerizable sphingolipid or glycospingolipid is a compound of the general structure:

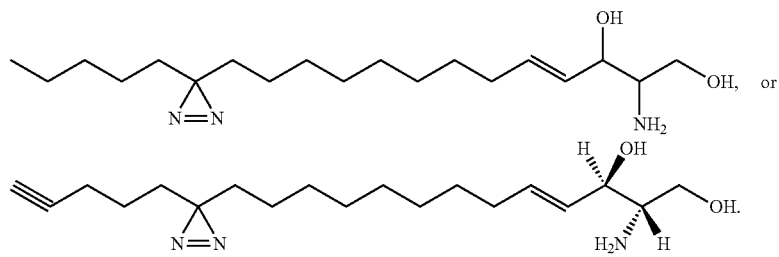

In one embodiment the liposome-forming lipids include, but are not limited to, phosphatidylcholine (PC), phosphatidylethanolamine (PE), phosphatidic acid (PA), phosphatidylglycerol (PG), phospatidylserine PS) and phosphatidylinositol (PI), and nonnatural lipid(s) and cationic lipid(s) such as DOTMA (N-(1-(2,3-dioxyloxy)propyl)-N,N,N-trimethyl ammonium chloride), distearoylPC, bis-SorbPC17,17, and 1,2-distearoyl-sn-glycero-3-phosphocholine (DSPC).

In one embodiment the liposome comprises one or more lipids selected from the group consisting of 1,2 dioleoyl-3-trimethylammonium-propane DOTAP, dioctadecyldimethylammonium chloride DODAc, 1,2-dimyristoyloxypropyl-3-dimethyl-hydroxyethyl ammonium DMRIE, 2,3-dioleoyloxy-N-(2(sperminecarboxamide)ethyl)-N,N-dimethyl-1 propananninium DOSPA, 1,2-dimethyl-dioctadecylammoniumbromide DDAB, 2-dioleyl-3-N,N,N-trimethylaminopropanechloride DOTMA, 1,2-dimyristoyl-3-trimethylammoniumpropane DMTAP, 1,2-distearoyl-3-trimethylammoniumpropane DSTAP, 1,2-Dioleoyl-3-dimethylammonium-propane DODAP, 1,2-dioleoyl-sn-glycero-3-phosphoethanolamine DOPE and N-(4-carboxybenzyl)-N,N-dimethyl-2,3-bis(oleoyloxy)propan-1-aminium DOBAQ and dioctadecylamidoglycylspermine DOGS.

In accordance with one embodiment a radiation triggered liposome is provided wherein the liposome comprises a standard liposome-forming lipid, and a polymerizable lipid bilayer component that accumulate primarily into lipid rafts, wherein the standard liposome-forming lipid is a phospholipid, including for example a phospholipid selected from the group consisting of phospatidylcholine, phosphatidylethanolamine, sphingomyelin, phosphatidic acid, phospatidylglycerol, phospatidylserine and phosphatidylinositol, and the polymerizable lipid bilayer component comprises
a) a steroid that has been modified to comprise a reactive group that upon activation by ionizing radiation forms covalent bonds with other components of the liposome,
b) a sphingolipid that has been modified to comprise a reactive group that upon activation by ionizing radiation forms covalent bonds with other components of the liposome, or
c) both a) and b). In one embodiment the liposome further comprises cholesterol molecules or cholesterol related compounds. In one embodiment the radiation triggered liposome of the present disclosure comprises 50-60% phospholipid, 20-25% cholesterol and 20-25% of a polymerizable lipid bilayer component, optionally wherein the polymerizable lipid bilayer component comprises 40-50% of polymerizable cholesterol and 50-60% polymerizable sphingolipid.

In one embodiment a radiation triggered liposome is provided wherein the liposome comprises 1,2-distearoyl-sn-glycero-3-phosphocholine (DSPC;), and a polymerizable sphingolipid of the general structure of Formula I:

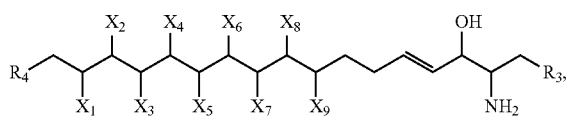

I wherein $X_1$-$X_9$ are independently H or a radiation activatable group;
$R_3$ is OH, phosphocholine, or phosphoenthanolamine; and
$R_4$ is —$CH_2CH_3$ or —CCH, with the proviso that 1, 2, or 3 of $X_1$-$X_9$ are a radiation activatable group with the remainder being H. In one embodiment the radiation activatable group is a diazirine group, and in a further embodiment only one of $X_1$-$X_9$ are a radiation activatable group, optionally a diazirine group. In a further embodiment the radiation triggered liposome also comprises a polymerizable steroid of the general structure of Formula II:

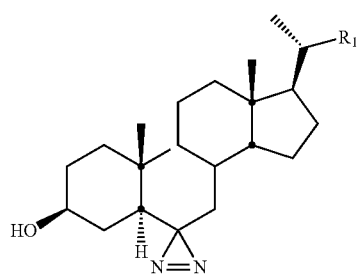

II wherein $R_1$ is selected from the group consisting of $C_1$-$C_8$, ($C_1$-$C_8$)OH, $(CH_2)_2COO(CH_2)_5CH_3$ and $(CH_2)_2COO(CH_2)_4CHCH$.

In one embodiment a radiation triggered liposome is provided comprising a 1,2-distearoyl-sn-glycero-3-phosphocholine (DSPC;), and a polymerizable sphingolipid of the general structure:

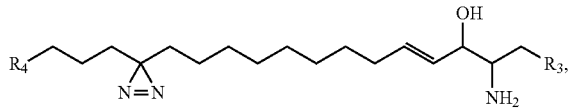

wherein
$R_3$ is OH, phosphocholine, or phosphoenthanolamine; and
$R_4$ is —$CH_2CH_3$ or —CCH; and a polymerizable steroid of the general structure of Formula II:

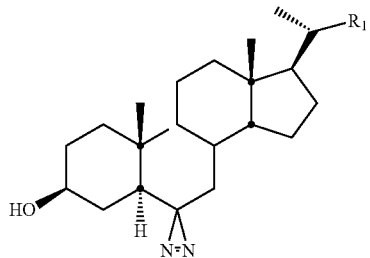

II wherein $R_1$ is selected from the group consisting of $C_1$-$C_8$, ($C_1$-$C_8$)OH, $(CH_2)_2COO(CH_2)_5CH_3$ and $(CH_2)_2COO(CH_2)_4CHCH$.

In a further embodiment a radiation triggered liposome is provided wherein the liposome comprises 1,2-distearoyl-sn-glycero-3-phosphocholine (DSPC;), Cholesterol, and a polymerizable sphingolipid of Formula I, optional with the addition of the polymerizable steroid of Formula II.

In one embodiment a liposome is provided that comprises
a phospholipid selected from the group consisting of phospatidylcholine, phosphatidyletheanolamine, sphingomyelin, phosphatidic acid, phospatidylglycerol, phospatidylserine and phosphatidylinositol; and
a polymerizable lipid component selected from the group consisting of
a) a polymerizable sphingolipid;
b) a polymerizable glycospingolipid;
c) a polymerizable steroid;
d) the combination of a) and b);
e) the combination of a) and c);
f) the combination of b) and c); or
g) the combination of a), b) and c), wherein
the polymerizable steroid is a compound of the general structure:

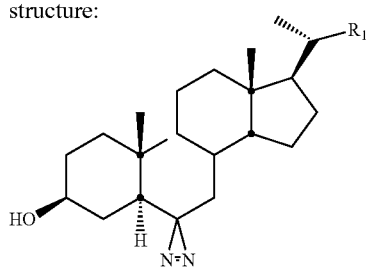

wherein $R_1$ is selected from the group consisting of $C_1$-$C_8$, ($C_1$-$C_8$)OH, $(CH_2)_2COO(CH_2)_4CH_3$ and $(CH_2)_2COO(CH_2)_4CH$; and the polymerizable sphingolipid or glycospingolipid is a compound of the general structure:

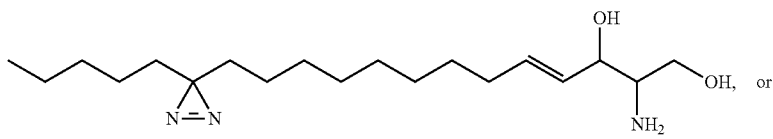

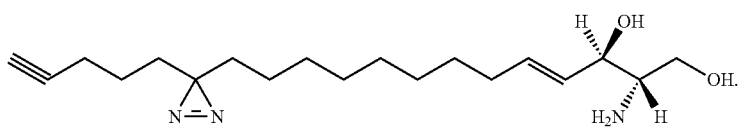

further wherein the total content of polymerizable lipid raft associated moieties is less than 30%, less than 25% or less than 20%.

The radiation triggered liposomes of the present disclosure can further comprise additional components known to those skilled in the art to stabilize the liposome. For example in one embodiment the radiation triggered liposome may include one or more polypeptides. In particular, proteins can be selected that are known to associate with the lipid rafts. The insertion of the proteins in the membrane will not only stabilize the lipid rafts but will enhance cross linking by exposing multiple linking sites to the polymerizable lipid raft associating moieties upon radiation exposure, hence supporting an increased membrane permeability and a more efficient drug release. In one embodiment the protein component of the radiation triggered liposomes is selected from the group consisting of the non-virulent part of the cholera toxin (cholera toxin subunit B) and lysenin.

In one embodiment a radiation triggered liposome is provided wherein the liposome comprises 1,2-distearoyl-sn-glycero-3-phosphocholine (DSPC;), and a polymerizable steroid having the structure:

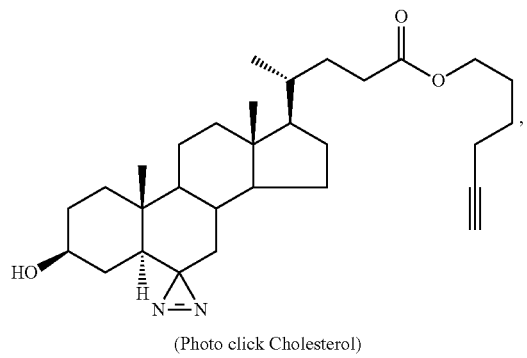 [SMILES: C#CCCCCOC(=O)CC[C@@H](C)[C@H]1CCC2C3CC4(N=N4)[C@H]4C[C@@H](O)CC[C@]4(C)C3CC[C@@]21C]

(Photo click Cholesterol)

and/or a polymerizable sphingolipid having the structure of

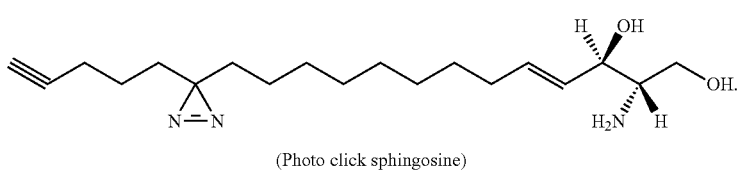 [SMILES: C#CCCCC1(CCCCCCCC/C=C/[C@@H](O)[C@@H](N)CO)N=N1]

(Photo click sphingosine)

Optionally the liposome further comprises cholesterol. In one embodiment a radiation triggered liposome is provided wherein the liposome comprises 1,2-distearoyl-sn-glycero-3-phosphocholine (DSPC;), Cholesterol, Sphingomyelin (SM), Photo click Cholesterol (P-Chol), and Photo click sphingosine (P-SM) at molar ratios 1:0.2:0.2:0.2:0.2.

In one alternative embodiment, any of the radiation triggered liposomes disclosed herein can further comprise a nano-scintillator. More particularly, a nano-scintillator is selected that is capable of emitting light within the range needed to enhance activation of the activatable group present on the polymerizable lipid raft associated moieties. In one embodiment the nano-scintillator is excited by ionizing radiation (e.g., X-radiation) and emits UV radiation. In one embodiment the nano-scintillator is a La(Ce)F nano-scintillator such as the $LaF_3Ce^{3+}$ water soluble nanoparticles made as described in Liu, Y. et al. Journal of Applied Physics 2008, 103, 063105 and Wang, C. et al. Journal of Applied Physics 2005, 97, 083506, both of which are incorporated herein by reference in their entireties. La(Ce)F nano-scintillators are known to emit strong UV light upon X-ray exposure and the ratios of the major components (La, Ce, and F) of the nano-scintillators can be altered to produce UV emittance optimal for excitation of the activatable groups present on the polymerizable moieties.

Those skilled in the art will appreciate that other nano-scintillators may be used in the compositions and methods described herein. For example, $LaF_3Tb^{3+}$ nano-scintillators have been described. The nano-scintillator chosen will determine the type of excitation source chosen for the compositions and methods of controlled drug delivery described herein. Choice of nano-scintillator will also depend on the choice of the activatable group, such that the nano-scintillator releases light within the wavelengths necessary to activate the activatable group.

In one alternative embodiment, any of the radiation triggered liposomes disclosed herein can be further modified to enhance their stability prior to being subjected to radiation. In one embodiment the radiation triggered liposomes are stabilized by coating their surface with a "stealth" material such as polyethylene glycol (PEG). PEGylated liposomes can not only prevent liposomes from fusing with one another but also enhance their in vivo circulation lifetime by suppressing plasma proteins from adsorbing onto the liposome. PEG can be covalently linked to the polar head groups of the phospholipids comprising the liposome using standard techniques known to those skilled in the art. Examples of PEG liposome compositions are various combinations of PEG and PCs, and/or PEs, and/or PAs, and/or PGs, and/or sterols such as cholesterol, and/or nonnatural lipids, and/or cationic lipids. In one embodiment of the present disclosure, the liposome(s) are comprised of $PEG_{2000}$-dioleoylPE, cholesterol, dioleoylPC, and bis-$SorbPC_{17,17}$. In another embodiment, the liposome(s) are comprised of $PEG_{2000}$-distearoylPE, cholesterol, distearoylPC, and bis-$SorbPC_{17,17}$. In yet another embodiment, the liposome(s) are comprised of $PEG_{2000}$-distearoylPE, distearoylPC.

In accordance with one embodiment, any of the radiation triggered liposomes disclosed herein can further comprise a therapeutic agent entrapped in the liposome, either embedded in the lipid bilayer or located in the aqueous lumen of the liposome. Examples of therapeutic agents include, but are not limited to, chemotherapeutics, biological response modifiers, biological cofactors, pharmaceuticals and radiopharmaceuticals, cell toxins, radiation sensitizers, and genetic materials. In one embodiment the entrapped therapeutic is a chemotherapeutic agent, an antibody, a toxin, or any combination thereof. In one embodiment the entrapped therapeutic is imiquinod.

The present disclosure also encompasses pharmaceutical compositions comprising any of the radiation triggered liposomes of the present disclosure and a pharmaceutically acceptable carrier. The pharmaceutical composition may include or be associated with an additional suitable pharmaceutical carrier or diluent. The releasable agent entrapped by the liposome may be a therapeutic or diagnostic agent. Carrying a therapeutic or diagnostic agent within or associated with a liposome provides for a biocompatible and non-toxic means of in vivo delivery. Chemotherapeutics, biological response modifiers, biological cofactors, pharmaceuticals and radiopharmaceuticals, cell toxins, radiation sensitizers, genetic materials, contrast agents, iodinated agents, fluorescent compounds, agents containing MRS/MRI sensitive nuclides, and the like, may be encapsulated in or associated with the liposomes of the present disclosure and released at desired target sites.

In another embodiment, a method of treating a condition responsive to a liposome-encapsulated or associated therapeutic agent is provided. The method comprises the steps of (i) administering to a patient a pharmaceutical composition comprising a radiation triggered liposomal delivery system comprising a therapeutic agent, wherein the therapeutic agent is encapsulated in or associated with any of the radiation triggered liposomes of the present disclosure, and a pharmaceutically acceptable carrier or diluent; and (ii) subjecting the patient to radiation in order to destabilize the liposome and release the therapeutic agent encapsulated in or associated with the liposome. In one embodiment, the radiation dosage ranges from about 5 to about 500 rads. In one embodiment, the radiation dosage ranges from about 50 to about 250 rads. Examples of therapeutic agents include, but are not limited to, chemotherapeutics, biological response modifiers, biological cofactors, pharmaceuticals and radiopharmaceuticals, cell toxins, radiation sensitizers and nucleic acids. Examples of conditions that are responsive to liposome-encapsulated or associated therapeutic agent(s) include, but are not limited to, cancer, immune disorders, developmental disorders, and genetic disorders.

Tumors represent a specific tissue site of considerable therapeutic interest; several research groups have reported the increased localization of sterically stabilized liposomes (PEG-liposomes) at tumor sites. The increased permeability of the vasculature at tumor sites (due to angiogenic factors secreted by tumors) allows liposomes to escape the capillaries to reach the tumor interstitial space. Sterically stabilized liposomes are more likely to accumulate at these sites because of their sustained concentration in the blood. Furthermore, it is known that the hydrophilic surface polymer may facilitate the transit from the capillaries to the tumor site. Reports of passive targeting of PEG-liposomes to tumors, including murine colon carcinomas, murine lymphomas, murine mammary carcinomas, human squamous cell lung carcinomas in SCID mice are known in the art. Specific targeting via antibodies coupled to liposomes has been observed as well. Antibody (mAb) conjugated sterically stabilized liposomes are known to localize at squamous cell carcinomas of the lung in mice and effectively deliver doxorubicin to these sites. Although the coupling of mAbs to conventional liposomes appears to increase their rate of clearance from the blood stream, the mAb conjugated PEG-liposomes, remain in circulation long enough to accumulate at their target cells. Accordingly, in one embodiment the radiation triggered liposomes of the present invention comprise an anti-cancer agent, including for example a chemotherapeutic agent or an immunotherapeutic composition, and optionally PEG polymers are adhered or linked to the external surface of the liposomes.

The present disclosure further contemplates a targetable liposomal delivery system, wherein said system comprises a radiation sensitive liposome and a therapeutic agent entrapped in said liposome, further wherein the liposome is targeted to a tumor site through attachment of at least one peptide to the liposome. The targeted radiation sensitive liposome comprises polymerizable lipid raft associating components in the liposomal membrane, a fraction of which polymerize upon exposure to ionizing radiation, thereby destabilizing the liposomal membrane and release of the liposomal contents. Peptides that target liposomes to tumor sites include, but are not limited to, peptide sequences, peptide fragments, antibodies, antibody fragments, and antigens.

In one embodiment a method of localized delivery of a therapeutic agent is provided. The method comprises the steps of administering to a patient in need of therapy, a composition comprising a radiation triggered liposome of the present disclosure. After passage of a sufficient amount of time to allow the administered radiation triggered liposomes to become concentrated at the target tissue, the target tissue is irradiated with ionizing radiation sufficient to affect activation of the reactive groups on the lipid raft associated compounds resulting in crosslinking of the lipid bilayer components and release of the lipid contents. The radiation triggered liposomes accumulate in the target tissues either passively or can be targeted to the desired location using techniques known to those skilled in the art.

Due to the ability to locally deliver chemotherapeutics to tumor cells, the presently disclosed radiation sensitive liposomes can be used to simultaneously administer radiation treatment and chemotherapeutic treatment to a cancer patient in need thereof. In accordance with one embodiment a method of enhancing ionizing radiation therapy in the treatment of cancer in a human patient is provided. The method comprises administering to the patient a radiation triggered liposome, wherein said liposome entraps an anti-cancer therapeutic, including for example an immunotherapeutic, chemotherapeutic or cytotoxic agent. The targeted tumor site of the patient is then subjected to a therapeutic dose of ionizing radiation therapy that destabilizes the membrane of the radiation triggered liposomes causing them to release the anti-cancer therapeutic at the targeted site to complement the therapeutic radiation therapy and enhance the efficacy of the ionizing radiation therapy.

In another embodiment of the present disclosure a method of producing a radiation sensitive liposomes is provided. The method encompasses drying the lipids that comprise the liposomes, hydrating the lipids with a buffer comprising agents to be encapsulated or associated in a desired molar ratio to create hydrated bilayers, converting the bilayers into liposomes, and purifying the liposomes. In one embodiment the lipids are dried in an oxygen free environment, such as an argon stream, and the bilayers are converted into liposomes by ultrasonification or freeze-thawing-extrusion. The liposomes may be purified with gel permeation chromatography or other methods.

In a further embodiment, a kit is provided for preparing radiation triggered liposomes of the present disclosure. The kit comprises a liposome forming lipid (e.g., a phospholipid) and a polymerizable lipid bilayer component that accumulates primarily into lipid rafts, wherein the lipid bilayer component has been modified to comprise a reactive group that is activated by ionizing radiation. In one embodiment the kit comprises a polymerizable sphingolipid or glycospingolipid having the general structure:

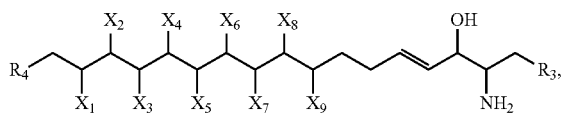

wherein $X_1$-$X_9$ are independently H or a radiation activatable group;
$R_3$ is OH, phosphocholine, phosphoenthanolamine, or a carbohydrate; and
$R_4$ is —$CH_2CH_3$ or —CCH, and a stable liposome-forming lipid selected from the group consisting of phosphatidylcholine (PC), phosphatidylethanolamine (PE), phosphatidic acid (PA), phosphatidylglycerol (PG), phospatidylserine PS) and phosphatidylinositol (PI), distearoylPC, bis-SorbPC17, 17, and 1,2-distearoyl-sn-glycero-3-phosphocholine (DSPC). In one embodiment the polymerizable sphingolipid or glycospingolipid having the general structure:

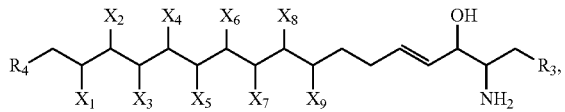

wherein 1, 2, or 3 of $X_1$-$X_9$ are radiation activatable group with the remainder being H;
$R_3$ is OH, phosphocholine, phosphoenthanolamine, or a carbohydrate; and
$R_4$ is —$CH_2CH_3$ or —CCH.
In a further embodiment the kit is provided with a compound of the general structure:

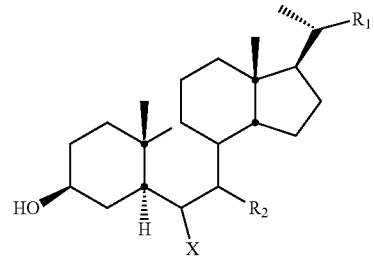

wherein X is a radiation activatable group;
$R_1$ is selected from the group consisting of $C_1$-$C_8$, ($C_1$-$C_8$)OH, ($CH_2CH_2CHOHCH(CH_3)_2$, $CH_2CH_2CH_2COH(CH_3)_2$, $CH_2CH_2CH_2CHOHCH_3$, $(CH_2)_2COO(CH_2)_5CH_3$ and $(CH_2)_2COO(CH_2)_4CHCH$, and
$R_2$ is H or OH.
In one embodiment the kit comprises a polymerizable lipid component selected from the group consisting of
a) a polymerizable sphingolipid;
b) a polymerizable glycospingolipid;
c) a polymerizable steroid;
d) the combination of a) and b);
e) the combination of a) and c);

f) the combination of b) and c); or
g) the combination of a), b) and c), wherein
the polymerizable steroid is a compound of the general structure:

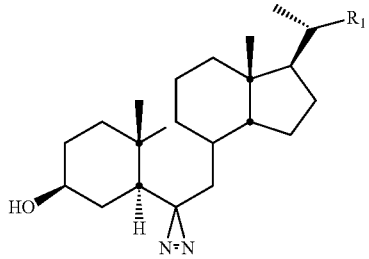

wherein $R_1$ is selected from the group consisting of $C_1$-$C_8$, $(C_1$-$C_8)OH$, $(CH_2)_2COO(CH_2)_4CH_3$ and $(CH_2)_2COO(CH_2)_4CH$; and the polymerizable sphingolipid or glycospingolipid is a compound of the general structure:

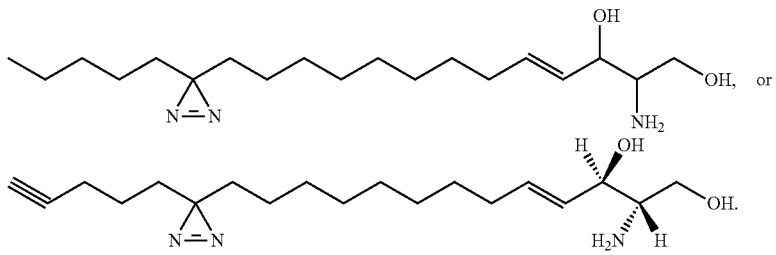

In one embodiment a kit is provided for preparing a radiation triggered liposomes of the present disclosure, wherein said kit comprises a phospholipid selected from the group consisting of phosphatidylcholine (PC), phosphatidylethanolamine (PE), phosphatidic acid (PA), phosphatidylglycerol (PG), phospatidylserine PS) and phosphatidylinositol (PI), distearoylPC, bis-SorbPC17,17, and 1,2-distearoyl-sn-glycero-3-phosphocholine (DSPC) and comprising a 1,2-distearoyl-sn-glycero-3-phosphocholine (DSPC;), a polymerizable sphingolipid of the general structure:

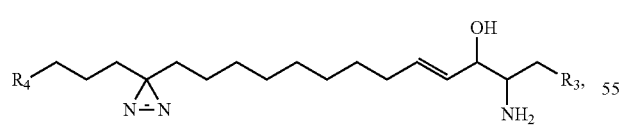

wherein
$R_3$ is OH, phosphocholine, or phosphoenthanolamine; and/or
$R_4$ is —$CH_2CH_3$ or —CCH; and a polymerizable steroid of the general structure of Formula II:

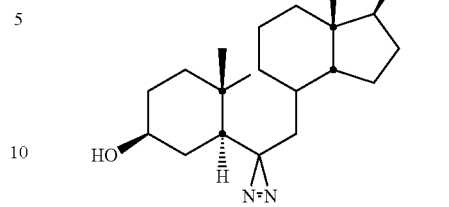

wherein $R_1$ is selected from the group consisting of $C_1$-$C_8$, $(C_1$-$C_8)OH$, $(CH_2)_2COO(CH_2)_5CH_3$ and $(CH_2)_2COO(CH_2)_4CHCH$.

In one embodiment a kit is provided for preparing a radiation triggered liposomes of the present disclosure, wherein said kit comprises a phospholipid selected from the group consisting of phosphatidylcholine (PC), phosphatidylethanolamine (PE), phosphatidic acid (PA), phosphatidylglycerol (PG), phospatidylserine PS) and phosphatidylinositol (PI), distearoylPC, bis-SorbPC17,17, and 1,2-distearoyl-sn-glycero-3-phosphocholine (DSPC) and comprising a 1,2-distearoyl-sn-glycero-3-phosphocholine (DSPC;), a polymerizable sphingolipid of the general structure:

a polymerizable sphingolipid of the general structure:

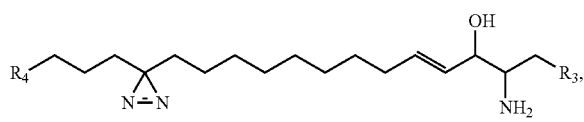

wherein
$R_3$ is OH and $R_4$ is —$CH_2CH_3$; and/or a polymerizable steroid of the general structure of Formula II:

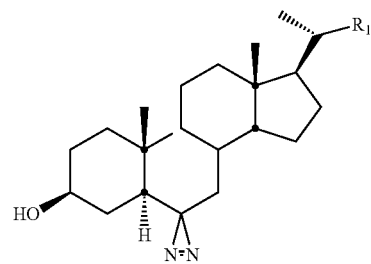

wherein $R_1$ is selected from the group consisting of $C_1$-$C_8$, ($C_1$-$C_8$)OH, and $(CH_2)_2COO(CH_2)_5CH_3$.

In one embodiment a kit is provided for preparing a radiation triggered liposomes of the present disclosure, wherein said kit comprises 1,2-distearoyl-sn-glycero-3-phosphocholine (DSPC;), and a polymerizable steroid having the structure:

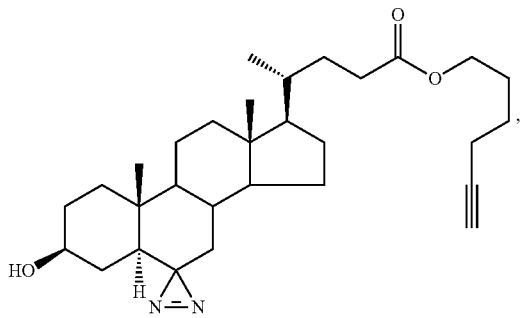

(Photo click Cholesterol)

and/or a polymerizable sphingolipid having the structure of

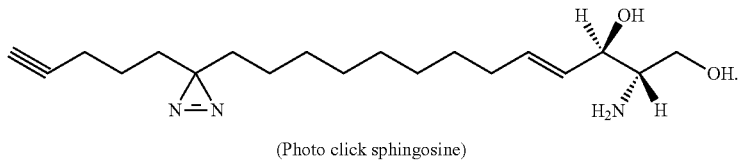 [SMILES: C#CCCCC1(CCCCCCCC/C=C/[C@@H](O)[C@@H](N)CO)N=N1]

(Photo click sphingosine)

Optionally the kit further comprises cholesterol.

In accordance with embodiment 1 a radiation triggered liposome is provided that is activated by radiation, including for example, ionizing X-ray irradiation. The liposome in one embodiment comprises a liposome-forming lipid and a polymerizable lipid component that accumulates into lipid rafts. At least some of the polymerizable lipid raft components have been modified to comprise a radiation activatable group that upon activation by radiation forms covalent bonds with other lipids of the liposome. Optionally, in accordance with embodiment 1, the radiation is ionizing radiation, including for example x-ray irradiation. Optionally, in accordance with embodiment 1, the ratio of the liposome-forming lipid to the polymerizable lipid component is selected from the group of ratios consisting of about 7:1, about 6:1, about 5:1, about 4:1 and about 3:1.

In one embodiment a liposome of embodiment 1 is provided wherein said polymerizable lipid component comprises
   a) a steroid that has been modified to comprise a radiation activatable group that upon activation by radiation forms covalent bonds with lipids of the liposome, or
   b) a sphingolipid that has been modified to comprise a radiation activatable group that upon activation by radiation forms covalent bonds with lipids of the liposome, or
   c) both a) and b).

In embodiment 3 a liposome of embodiment 1 or 2 is provided wherein said liposome-forming lipid is a phospholipid selected from the group consisting of phospatidylcholine, phosphatidylethanolamine, phosphatidic acid, phospatidylglycerol, phospatidylserine, phosphatidylinositol and 1,2-distearoyl-sn-glycero-3-phosphocholine (DSPC).

In embodiment 4 a liposome of any one of embodiments 1-3 is provided wherein the liposome further comprises cholesterol.

In embodiment 5 a liposome of any one of embodiments 1-4 is provided further comprising a protein.

In embodiment 6 a liposome of any one of embodiments 1-5 is provided wherein the liposome further comprises a protein that comprises the non-virulent part of the cholera toxin (cholera toxin subunit B) or lysenin.

In embodiment 7 a liposome of any one of embodiments 1-6 is provided wherein said polymerizable lipid component is selected from the group consisting of a compound of the structure:

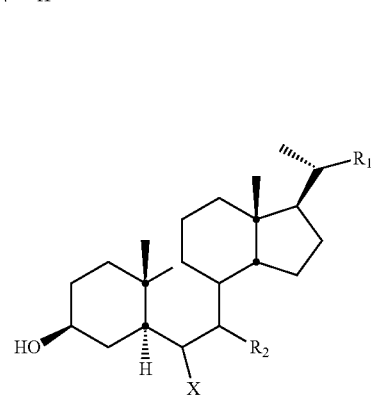

wherein X is a radiation activatable group;
$R_1$ is selected from the group consisting of $C_1$-$C_8$, ($C_1$-$C_8$)OH, $(CH_2CH_2CHOHCH(CH_3)_2$, $CH_2CH_2CH_2COH(CH_3)_2$, $CH_2CH_2CH_2CHOHCH_3$, $(CH_2)_2COO(CH_2)_5CH_3$ or $(CH_2)_2COO(CH_2)_4CHCH$, and $R_2$ is H or OH; and
a compound of the general structure:

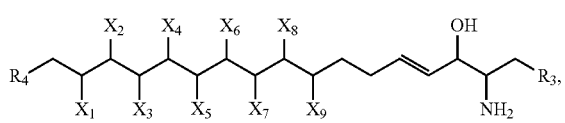

wherein 1, 2, or 3 of $X_1$-$X_9$ are radiation activatable groups with the remainder being H;
$R_3$ is OH, phosphocholine, phosphoenthanolamine, or a carbohydrate; and
$R_4$ is —$CH_2CH_3$ or —CCH.

In embodiment 8 a liposome of any one of embodiments 1-7 is provided wherein the radiation activatable group is a diazirine.

In embodiment 9 a liposome of any one of embodiments 1-8 is provided wherein said polymerizable lipid component is a polymerizable steroid having the general structure of Formula II:

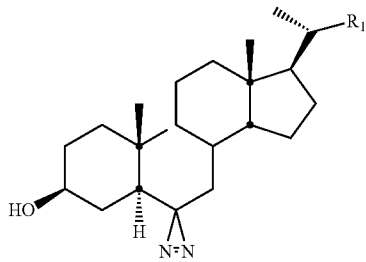

II wherein $R_1$ is selected from the group consisting of $C_1$-$C_8$, $(C_1$-$C_8)OH$, $(CH_2)_2COO(CH_2)_5CH_3$ or $(CH_2)_2COO(CH_2)_4CHCH$; or a polymerizable sphingolipid having the general structure of:

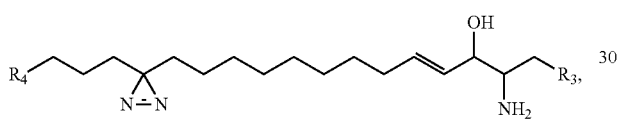

wherein $R_3$ is OH, phosphocholine, or phosphoenthanolamine; and $R_4$ is —$CH_2CH_3$ or —CCH.

In embodiment 10 a liposome of any one of embodiment 1-9 is provided wherein said polymerizable lipid is a compound of the structure:

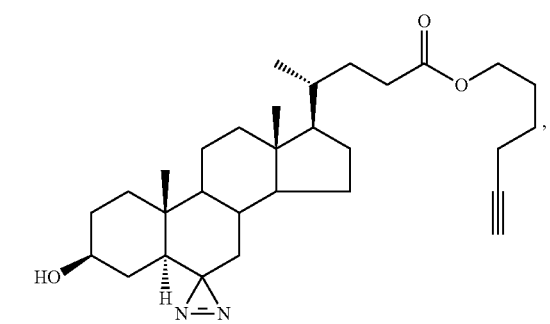

(Photo click Cholesterol)

or has the structure of

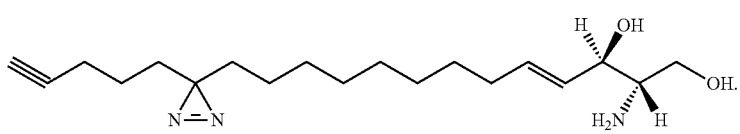

(Photo click sphingosine)

In embodiment 11 a liposome of embodiment of any one of embodiments 1-10 is provided wherein the liposome comprises 1,2-distearoyl-sn-glycero-3-phosphocholine (DSPC;), Cholesterol, Sphingomyelin (SM), Photo click Cholesterol (P-Chol), and Photo click sphingosine (P-SM), optionally at molar ratios 1:0.2:0.2:0.2:0.2.

In embodiment 12 a liposome of any one of claims 1-11 is provided further comprising a pharmaceutical agent, optionally an anticancer agent, entrapped by said liposome.

In embodiment 13 a liposome of any one of embodiments 1-12 is provided where in the liposome comprises an anticancer agent, entrapped by said liposome, wherein the anticancer agent is a chemotherapeutic agent or an immunotherapeutic composition.

In embodiment 14 a liposome of any one of claims 1-13 is provided wherein the radiation activatable group is activated by exposure to ionizing X-ray radiation.

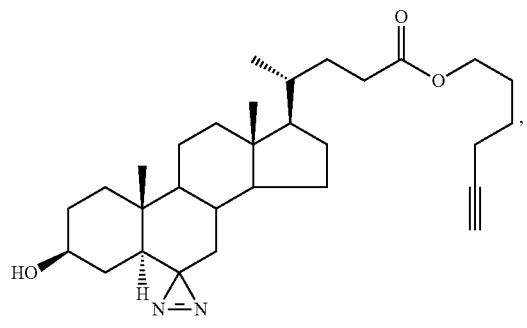

(Photo click Cholesterol)

or the structure of

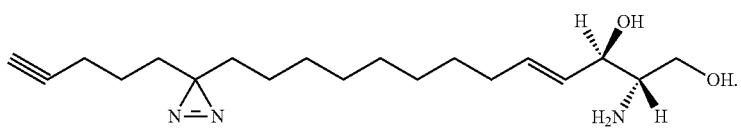

(Photo click sphingosine)

In embodiment 15 a liposome of any one of claims 1-14 is provided wherein the liposome has a diameter within the range of about 50 to 250 nm, optionally about 75 to about 200 nm, optionally about 100 to 250 nm, optionally about 150 to 250 nm, optionally about 50 to 150 nm.

In embodiment 16 a liposome of any one of claims 1-15 is provided wherein the liposome further comprises a targeting molecule on the external surface of the liposome.

In embodiment 17 a liposome of any one of claims 1-16 is provided wherein the liposome further comprises a nano-scintillator capable of emitting UV light upon excitation by radiation.

In embodiment 18 a liposome of any one of embodiments 1-17 is provided wherein the activating radiation is X-radiation.

In embodiment 19 a kit for preparing a radiation triggered liposome is provided comprising the components of the liposomes of any one of embodiments 1-18, optionally wherein the kit is provided with a liposome-forming lipid selected from the group consisting of phospatidylcholine, phospatidylethanolamine, sphingomyelin, phosphatidic acid, phospatidylglycerol, phospatidylserine and phospatidylinositol and a) a steroid that has been modified to comprise a reactive group that upon activation by radiation forms covalent bonds with lipids of the liposome, and/or b) a sphingolipid that has been modified to comprise a reactive group that upon activation by radiation forms covalent bonds with lipids of the liposome, optionally wherein the kit comprises a polymerizable lipid having the structure:

In embodiment 20 a method of enhancing ionizing radiation therapy in the treatment of cancer in a human patient, said method comprising:
administering to the patient a radiation triggered liposome of any one of embodiments 1-18, wherein said liposome comprises an anti-cancer therapeutic entrapped within the lumen of the liposome;
administering the ionizing radiation therapy to target a tumor site of the patient; thereby destabilizing the membrane of said administered radiation triggered liposome to release the anti-cancer therapeutic at the targeted site to complement the therapeutic radiation therapy and enhance the efficacy of the ionizing radiation therapy. The method of embodiment 20 wherein the ionizing radiation therapy comprises the administration of X-rays or gamma rays.

Example 1

Liposomes for UV and X-Ray Triggered Drug Release

The long term goal of this approach is to achieve the release of antineoplastic drugs loaded into liposomes previously accumulated into tumors by the enhanced permeability and retention effect or direct targeting. To enhance the efficacy of the treatment, we propose to trigger the release of the drug by using X-ray or other ionizing radiation currently employed for the radiotherapy treatment scheme. The simultaneous highly localized chemo and radiotherapy is expected to provide supra-activity, i.e. an improved efficacy than what would be obtained by non-concomitant combined treatments, while minimizing the remote toxicity arising from a systemic distribution of the drug. In this endeavor, we propose using liposomes specially designed to release their payload when exposed to actinic beams. To achieve this goal, we designed the liposomes to include photo click components that respond to UV light by cross linking.

Previous work from other groups indicates that a more rigid membrane realized by cross-linking a small amount of photo-polymerizable lipids increases permeability to drug-like molecules. We propose using photo click cholesterol and photo click sphingosine to produce radiation-sensitive liposome membrane. Unlike approaches comprising other photo-sensitive lipids, these compounds accumulate primarily into lipid rafts, which significantly facilitate cross linking upon exposure to radiation and are anticipated to lead to an improved efficacy with respect to drug release. Moreover, addition of raft-targeting proteins may further contribute to raft stabilization therefore improved cross linking and release upon radiation exposure.

Figure 1B:
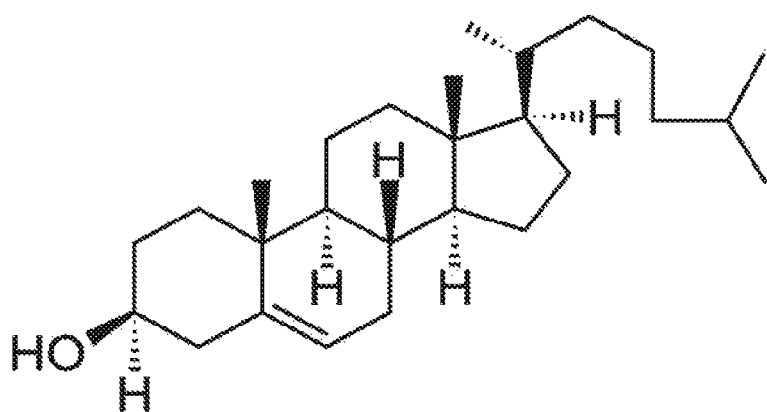
Figure 1C:
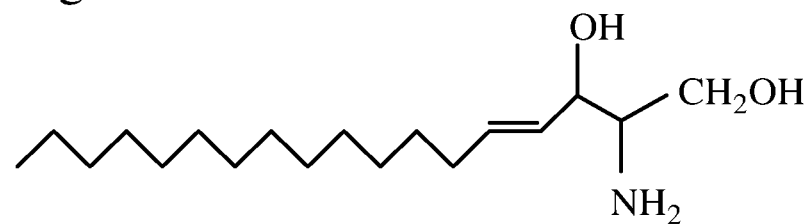
Figure 2A:
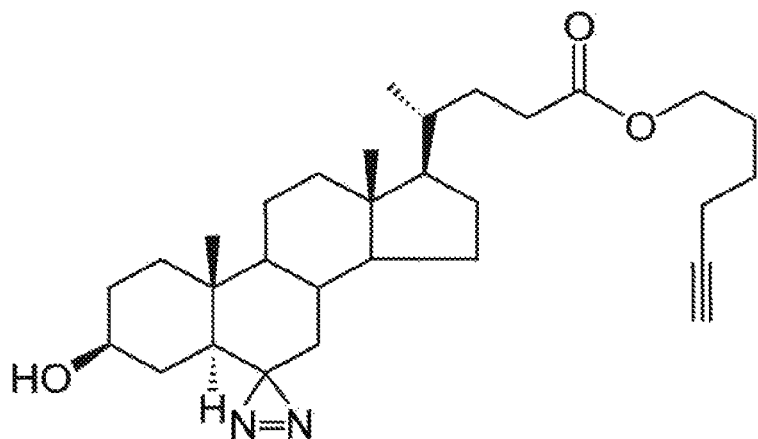
FIGS. 2A & 2B provides the structures of the crosslinking lipid bilayer components Photo click Cholesterol (P-Chol.
Figure 2B:

Materials and Methods 1,2-distearoyl-sn-glycero-3-phosphocholine (DSPC;), Cholesterol (Chol), Sphingomyelin (SM), Photo click Cholesterol (P-Chol), and Photo click sphingosine (P-SM) have been dissolved in chloroform at molar ratios 1:0.2:0.2:0.2:0.2. The structure of each of those compounds is provided in FIGS. 1 and 2. The mixture was vacuum dried for 48 hours and hydrated with 135 mM NaCl, 20 mM Hepes (pH7), and 30 mM calcein (self-quenching concentration). The final concentration of DSPC in the hydration buffer was 10 mg/mL. A control sample consisted of DSPC, Chol, and SM only (1:0.4:0.4 molar ratio).

Results and Discussion

UV-Induced Dye Release

100 µL of liposome suspension was mixed with 1.9 mL dye-free buffer and placed in the sample holder of the fluorometer set for calcein measurement. UV-excitation (365 nm) was provided from an UV-LED placed above the cuvette. The release of the dye was estimated by monitoring the increase of fluorescence recorded when the trapped calcein was released into the bulk through the permeabilized liposomal membrane upon UV exposure. The fluorescence signal was normalized to 1 (100%) by considering the magnitude of the fluorescence signal recorded upon complete membrane breach achieved by addition of Triton X100.

Figure 3:
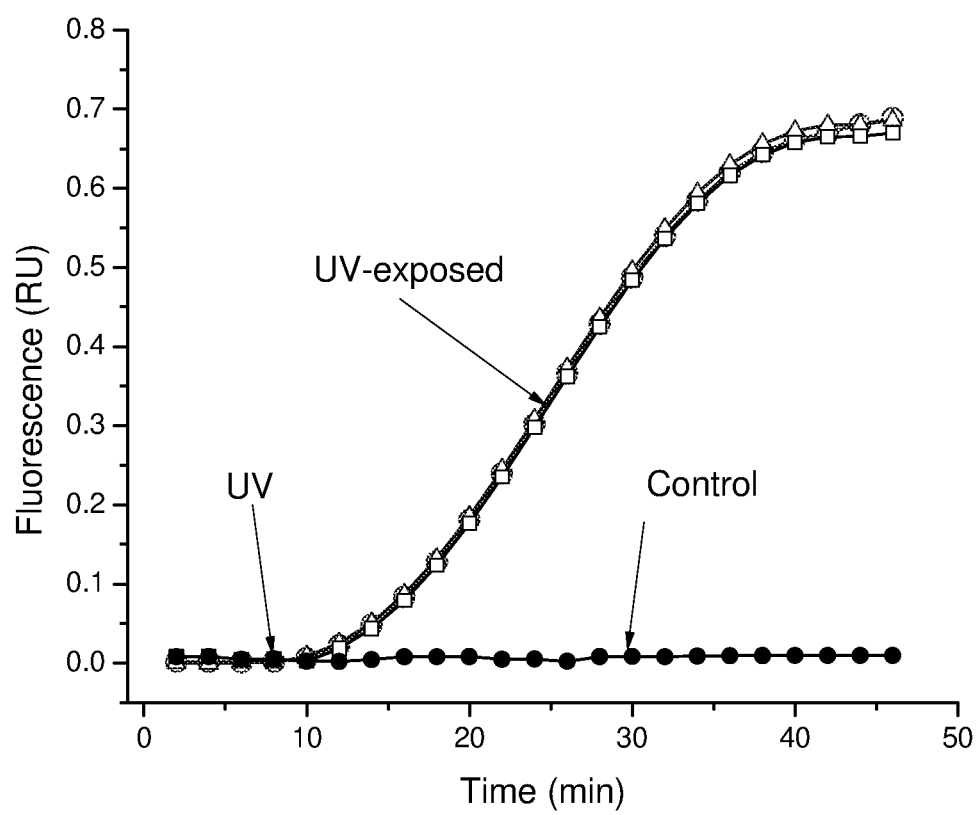
FIG. 3 is a graph representing data obtained for dye release from UV-sensitive liposomes. Liposomes comprising photo click compounds showed a sustained release, and the liposomes devoid of the photo click compounds were unresponsive to exposure.

The results of three independent experiments is presented in FIG. 3. In less than 2 minutes after UV exposure, the dye leakage was recorded as increase in fluorescence, while the control sample showed no release.

The sigmoidal curve suggests a multistep process which most probably starts by a limiting step of crosslinks production. For this experiment, the liposomes were continuously exposed to the UV light but it is expected the exposure to be required only for completion of the cross-linking process. A ~70% drug release was recorded for the time frame of the experiment; we expect an increase of this efficiency by further stabilization of the lipid rafts with targeting proteins. Nano-scintillators

CONCLUSIONS

Our experiments clearly show that UV-light may be used to directly breach photo click liposomes for drug delivery purposes. Also, the work suggests that drug release from liposomes may be achieved by using X-ray as a trigger by down converting the ionizing radiation to UV via nano-scintillators encased into liposomes.

Example 2

X-Ray Triggered Release of Liposomal Content

Liposomes comprising a polymerizable lipid component of the present disclosure were investigated for their ability to release encapsulated calcein upon exposure to X-rays.

Materials and Methods

1. Calcein Self-Quenching Experiment

A stock solution of calcein was serially diluted for a final concentration ranging from 0.01 mM to 50 mM in a 50 mM KCl solution buffered with 50 mM Hepes (pH 7.2). 4 mL of calcein solution was placed in a cuvette and the fluorescence measured with a Fluoromax 4 spectrometer (Horiba). The excitation wavelength was set to 490 nm (slit width 0.5 nm) and the spectrum was recorded between 505 nm and 580 nm (1 nm increment, 0.5 nm slit width, 1 second integration time).

The calcein fluorescence was measured at 512 nm for all samples after background correction. A fluorescence vs concentration plot demonstrated that calcein self-quenching manifests in these experimental conditions at concentrations that exceeds ~0.02 mM.

Liposome Preparation

Liposomes loaded with calcein were produced by extrusion with an Avanti Polar Lipids extruder. The lipids (1,2-distearoyl-sn-glycero-3-phosphocholine (DSPC), Cholesterol (Chol), Sphingomyelin (SM), Photo click Cholesterol (PChol), Photo click sphingosine (PSM), and 1,2-distearoyl-sn-glycero-3-phosphoethanolamine-N-lmethoxy(polyethylene glycol)-20001 (DSPEPEG)) were purchased as powders from Avanti Polar Lipids and dissolved in chloroform at molar ratios 1:0.25:0.2:0.2:0.25:0.05. The lipid mixture was dried under vacuum for 48 hours and hydrated with 50 mM KCl, 50 mM Hepes (pH 7.2), and 35 mM calcein (self-quenching concentration). The final concentration of DSPC in the hydration buffer was 10 mg/mL. A control sample consisted of liposomes made with DSPC, DSPEPEG, Chol, and SM only (the same molar ratios).

The thin lipid film was hydrated in the same buffered ionic solution for 4 hours at 55° C. After hydration, 800 nm liposomes were produced by extrusion through stacked polycarbonate filters mounted in the extruder. Upon completing 40 extrusion cycles, the liposome solution was additionally extruded for 50 more cycles through 200 nm filters at 72° C.; the polydispersity was assessed by Dynamic Light Scaterring (Malvern-ZetaSizer). The non-incorporated calcein was removed by extended dialysis in cassettes (ThermoFisher, 250 kDa cutoff) against 2 L of ionic buffer and the samples kept in amber vials in a refrigerator for further use.

X-Ray Exposure

For further investigations, 100 µL of liposome suspension was mixed with 2.9 mL dye-free ionic buffer and the spectrum recorded with the fluorometer. Four samples and negative controls were exposed to X-ray using an X-ray imaging system. The control parameters were set as follows: 0.125 MeV, 320 mA, and 20 pulses. After exposure, the experimental samples were transferred for calcein release analyses with the fluorometer by recording the resulting spectrum at different time intervals (~10 mins) and using the fluorescence measured before radiation exposure as baseline. The release efficiency E was calculated by considering the fluorescence of the sample before exposure ($F_0$), the fluorescence of the sample after exposure and at different time intervals (F), and the maximal fluorescence ($F_{100}$) determined upon total release of calcein from liposomes in the presence of Triton X100. The formula used for the plot presented in FIG. 3 is:

$$E=(F-F_0)/(F_{100}-F_0)$$

Figure 4:
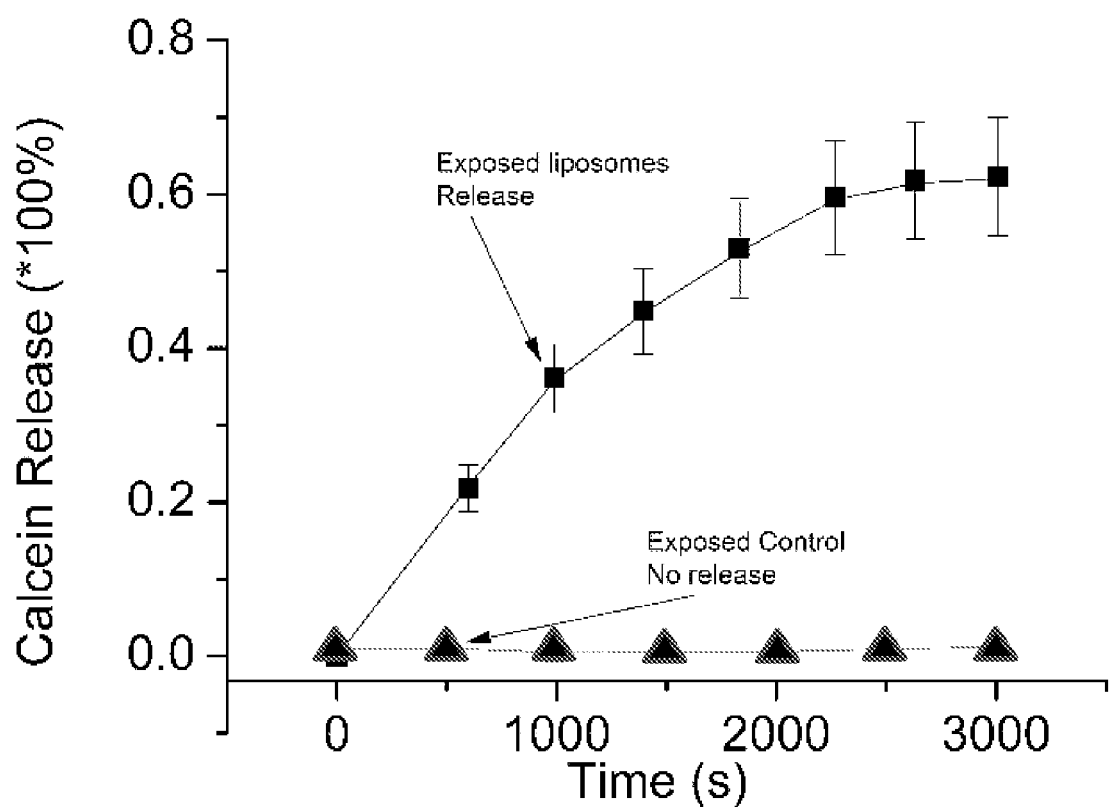
FIG. 4 is a graph demonstrating X-ray induced release of calcein from liposomes comprising photo click compounds. Control liposomes (▲) lacking lipid raft forming polymerizable lipid compounds did not show calcein release upon exposure to X-ray. In contrast, sustain release was presented by liposomes comprising lipid raft forming polymerizable lipid compounds (■), which reached ~63% in 3000 secs.

No statistical difference was observed between the fluorescence data for exposed and non-exposed control samples, which did not contain a polymerizable lipid component (e.g., photo click lipids). However, the X-ray sensitive liposomes presented a sustained release (FIG. 4), which reached ~63% in less than one hour.

Example 3

Figure 5:
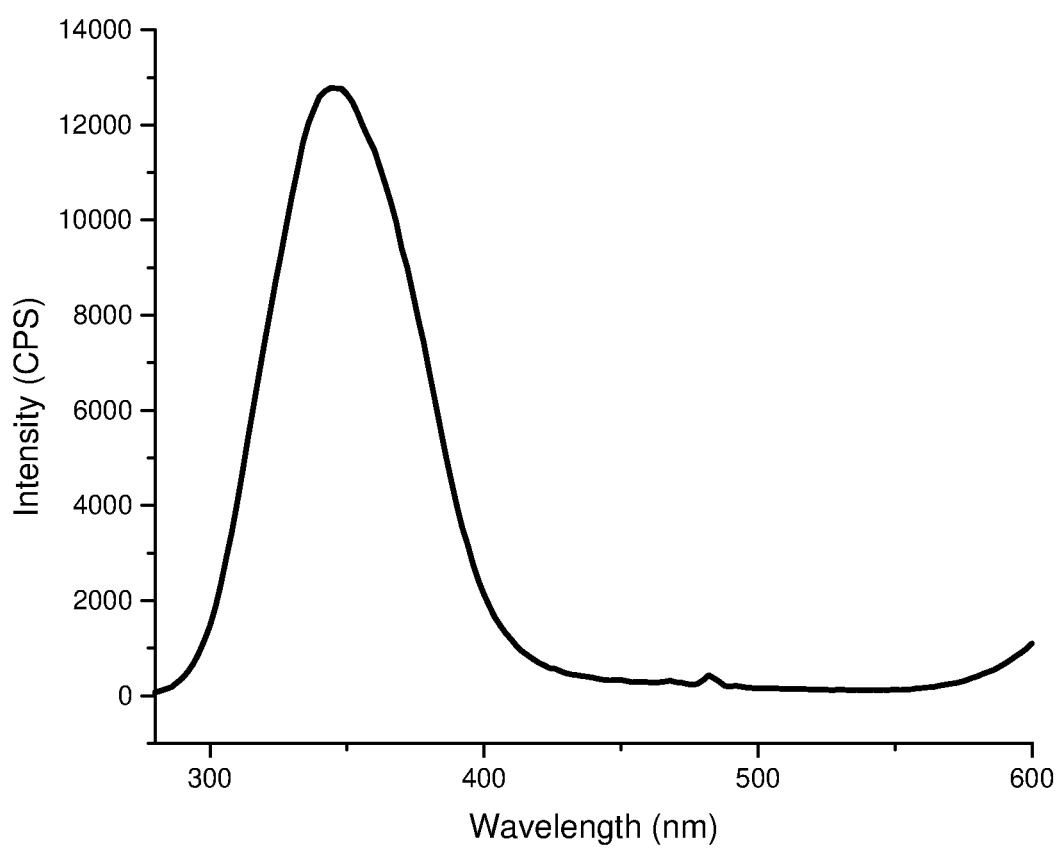
FIG. 5 is a graph of the UV emission from X-ray fluorescence of nanoscintillator particles ($La_{0.7}(F)_3Ce_{0.3}$). The nanoparticles were prepared by following the procedure of Liu et al (J. Appl. Phys, 103, 063105 (2008)). Briefly, 20 mM $NH_4F$ solution was added dropwise over 15 mL of $La(NO_3)_3$ and $Ce(NO_3)_3$ mixture (pH 7.4) in the indicated molar ratios at room temperature, for several hours and under continuous stirring. The addition of $NH_4F$ was stopped once a turbid suspension started to form in the reaction tube. The nanoparticles were centrifuged at high speed, washed with deionized water five times, re-suspended in an ionic buffer (pH 7.4) and filtered through Wathman nucleopore filters (30 nm pore diameter).

As shown by the data presented in Example 1, dye release may be initiated by UV exposure. However, the human body is not transparent to UV (or visible) light, therefore limiting the utility of UV activation. An additional method of supplementing liposomal release upon irradiation is to use La(Ce)F nano-scintillators, which emit strong UV light upon X-ray exposure. To provide evidence for this approach, we prepared three nano-scintillator samples comprising different ratios of the major components (La, Ce, and F) of the nano-scintillators. When exposed to X-ray radiation, all samples presented a strong luminescence in the UV region of interest (See FIGS. 5A-5C). Samples a) and b) (FIGS. 5A & 5B) showed an extended luminescence in the visible range and even sharp peaks in the blue region. Sample c) presented a luminescence spectrum centered at around 350 nm, a low luminescence in the visible region, and a much stronger signal at 365 nm than the other two samples (FIG. 5C). Therefore, the composition of sample c) seems to be the most suitable for drug release upon X-ray exposure.

What is claimed is:

1. A radiation triggered controlled release liposome, said liposome comprising
    a liposome-forming lipid, and
        a polymerizable lipid component that accumulates into lipid rafts, said polymerizable lipid component comprising
        a) a steroid that has been modified to comprise a radiation activatable group that upon activation by radiation forms covalent bonds with lipids of the liposome, or
        b) a sphingolipid that has been modified to comprise a radiation activatable group that upon activation by radiation forms covalent bonds with lipids of the liposome, or
        both a) and b);
        wherein said polymerizable lipid component upon activation by radiation forms covalent bonds with other lipids of the liposome, and induces release of the liposome contents.
2. The liposome of claim 1, wherein said polymerizable lipid component comprises a polymerizable sphingolipids or a polymerizable glycospingolipid.
3. The liposome of claim 1, wherein said liposome-forming lipid is a phospholipid selected from the group consisting of phospatidylcholine, phosphatidylethanolamine, phosphatidic acid, phospatidylglycerol, phospatidylserine, phosphatidylinositol and 1,2-distearoyl-sn-glycero-3-phosphocholine (DSPC).
4. The liposome of claim 1, wherein the liposome further comprises cholesterol.
5. The liposome of claim 1, further comprising a protein.
6. The liposome of claim 5, wherein the protein is the non-virulent part of the cholera toxin (cholera toxin subunit B) or lysenin.
7. The liposome of claim 1, wherein said polymerizable lipid component comprises a compound selected from the group consisting of a compound of the structure:

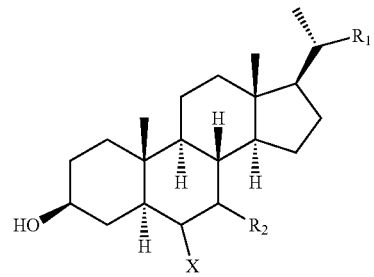

wherein X is a radiation activatable group;
$R_1$ is selected from the group consisting of $C_1$-$C_8$, ($C_1$-$C_8$) OH, ($CH_2CH_2CHOHCH$ ($CH_3$)$_2$, $CH_2CH_2CH_2COH$ ($CH_3$)$_2$, $CH_2CH_2CH_2CHOHCH_3$, ($CH_2$)$_2$COO ($CH_2$)$_5CH_3$ or ($CH_2$)$_2$COO ($CH_2$)$_4$CCH, and $R_2$ is H or OH; and
a compound of the general structure:

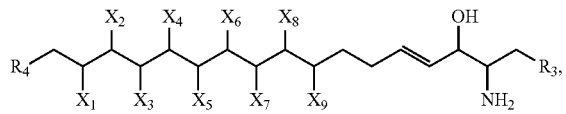

wherein 1, 2, or 3 of $X_1$-$X_9$ are radiation activatable groups with the remainder being H;
$R_3$ is OH, phosphocholine, phosphoenthanolamine, or a carbohydrate; and
$R_4$ is-$CH_2CH_3$ or —CCH.
8. The liposome of claim 7, wherein the radiation activatable group is a diazirine.
9. A radiation triggered liposome, said liposome comprising
    a liposome-forming lipid, and
    a polymerizable lipid component wherein said polymerizable lipid component comprises a compound selected from the group consisting of a polymerizable steroid having the general structure of Formula II:

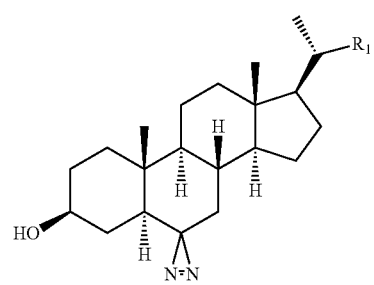

wherein $R_1$ is selected from the group consisting of $C_1$-$C_8$, ($C_1$-$C_8$) OH, ($CH_2$)$_2$COO ($CH_2$)$_5CH_3$ or ($CH_2$)$_2$COO ($CH_2$)$_4$CCH; and a polymerizable sphingolipid having the general structure of:

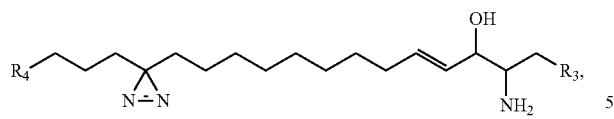

wherein
R₃ is OH, phosphocholine, or phosphoenthanolamine; and
R₄ is -CH₂CH₃ or —CCH.

10. The liposome of claim 9, wherein said polymerizable steroid is a compound of the structure:

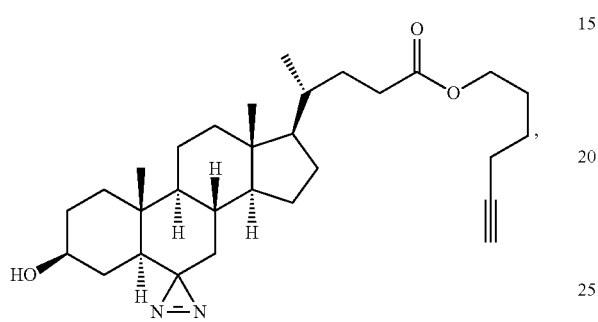

(Photo click Cholesterol)

and the polymerizable sphingolipid has the structure of

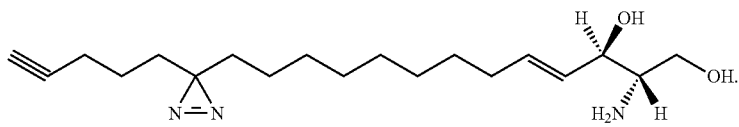

(Photo click sphingosine)

11. The liposome of claim 1, wherein the liposome comprises 1,2-distearoyl-sn-glycero-3-phosphocholine (DSPC;), Cholesterol, Sphingomyelin (SM), Photo click Cholesterol (P-Chol), and Photo click sphingosine (P-SM) at molar ratios 1:0.2:0.2:0.2:0.2.

12. The liposome of claim 1, further comprising an anticancer agent entrapped by said liposome.

13. The liposome of claim 12, wherein the anticancer agent is a chemotherapeutic agent or an immunotherapeutic composition.

14. The liposome of claim 1, wherein the radiation activatable group is activated by exposure to ionizing X-ray radiation.

15. The liposome of claim 1, having a diameter within the range of about 50 to 250 nm.

16. The liposome of claim 1, wherein the liposome further comprises a targeting molecule on the external surface of the liposome.

17. The liposome of claim 1, wherein the liposome further comprises a nano-scintillator capable of emitting UV light upon excitation by radiation.

18. The liposome of claim 17, wherein said radiation is X-ray radiation.

19. A kit for preparing a radiation triggered liposome, said kit comprising
- a liposome-forming lipid selected from the group consisting of phospatidylcholine, phosphatidylethanolamine, sphingomyelin, phosphatidic acid, phospatidylglycerol, phospatidylserine and phospatidylinositol and
- a) a steroid that has been modified to comprise a reactive group that upon activation by radiation forms covalent bonds with lipids, and/or
- b) a sphingolipid that has been modified to comprise a reactive group that upon activation by radiation forms covalent bonds with lipids.

20. A method of enhancing ionizing radiation therapy in the treatment of cancer in a human patient, said method comprising:
- administering to the patient a radiation triggered liposome of claim 1, wherein said liposome entraps an anti-cancer therapeutic;
- administering the ionizing radiation therapy to target a tumor site of the patient; thereby destabilizing the membrane of said administered radiation triggered liposome to release the anti-cancer therapeutic at the targeted site to complement the therapeutic radiation therapy and enhance the efficacy of the ionizing radiation therapy.

* * * * *